United States Patent [19]

Starke et al.

[11] 4,009,020
[45] Feb. 22, 1977

[54] METHOD OF REGULATING PLANT GROWTH

[75] Inventors: George Robert Starke, Perkasie; Anson Richard Cooke, Hatfield, both of Pa.

[73] Assignee: Amchem Products, Inc., Ambler, Pa.

[22] Filed: May 6, 1975

[21] Appl. No.: 574,990

[52] U.S. Cl. .................................. 71/76; 71/94
[51] Int. Cl.$^2$ ................................. A01N 5/00
[58] Field of Search .......................... 71/94, 76

[56] References Cited

UNITED STATES PATENTS

| | | | |
|---|---|---|---|
| 3,317,542 | 5/1967 | Haszeldine et al. | 71/94 |
| 3,438,993 | 4/1969 | Wilbert et al. | 71/94 |
| 3,837,836 | 9/1974 | Diehl et al. | 71/94 |

FOREIGN PATENTS OR APPLICATIONS

| | | | |
|---|---|---|---|
| 47-16477 | 9/1972 | Japan | 71/94 |
| 923,387 | 4/1963 | United Kingdom | 71/94 |

OTHER PUBLICATIONS

Campbell et al., "Studies in the Quinoline Series" (1946) J.A.C.S. 68 pp. 1837-1840 (1946).
Senear et al., "The Synthesis of Potential Antimalarials etc." (1946) J.A.C.S. 68 pp. 2695-2697 (1946).
Pinder et al., "Antimalarials II α-(2-piperidyl) etc." (1967) J. Med. Chem. 11 pp. 267-269 (1968).

*Primary Examiner*—Glennon H. Hollrah
*Attorney, Agent, or Firm*—Ernest G. Szoke; Michael E. Zall; Ruth S. Moyerman

[57] ABSTRACT

A method for producing a growth regulating effect in a plant which comprises applying to the plant an effective amount, with respect to the plant being treated, of cinchoninic acid or a derivative thereof.

56 Claims, No Drawings

METHOD OF REGULATING PLANT GROWTH

This invention relates to the use of cinchoninic acid and certain derivatives thereof to produce growth regulating responses in plants. Cinchoninic acid is 4-quinoline carboxylic acid, that is to say:

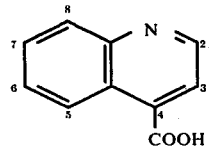

the quinoline nucleus being numbered as shown. It has been found that, as well as cinchoninic acid itself, the method of the invention may also employ a substituted cinchoninic acid having a molecular structure in which the quinoline nucleus has attached thereto hydrogen in the 3-position and a substituent in the 2-position selected from the group consisting of:
a. halo,
b. cyano,
c. nitro,
d. lower alkyl,
e. perhalo-(lower alkyl),
f. phenyl,
g. halo-substituted phenyl, and
h. carboxyl, as well as functional derivatives of these compounds. The effect on the activity of substituents in the 5-, 6-, 7- and 8-position is limited, and cinchoninic acid derivatives having a wide variety of substituents in the 5-, 6-, 7- and 8-positions may be employed in the method of this invention.

Similarly a large number of functional derivatives of cinchoninic acid and the above-described substituted cinchoninic acids may be employed in this invention. By the term functional derivatives as applied to the various cinchoninic acids there is meant derivatives of both the carboxyl group at the 4-position (and at the 2-position, when appropriate) and the heterocyclic nitrogen. Thus, examples of functional derivatives which may be used in this invention include the nitriles, esters, amides (substituted and unsubstituted), halides and salts of the acid function, the various thioacid analogues of these compounds, and acid salts of the basic heterocyclic nitrogen.

Amongst the compounds which may be used in the invention, the preferred cinchoninic acid derivatives are those falling within the general formula:

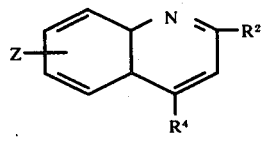

wherein:
Z is selected from the group consisting of:
a. hydrogen, and
b. halo;
$R^2$ is selected from the group consisting of:
a. hydrogen,
b. halo,
c. cyano,
d. nitro,
e. lower alkyl,
f. perhalo-(lower alkyl),
g. phenyl,
h. halo-substituted phenyl, and
i. carboxyl; and
$R^4$ is selected from the group consisting of:
a. cyano, and

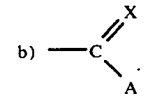

wherein X is selected from the group consisting of:
i. oxygen, and
ii. sulphur,
A is selected from the group consisting of:
i. XR
ii. NRR', and
iii. halo, and
R and R' are independently selected from the group consisting of:
i. hydrogen,
ii. lower alkyl, and
iii. lower aryl,
together with agriculturally-acceptable salts thereof.

Where the term "halo" is used herein, it is to be understood to mean the familiar halogens, i.e., fluorine, chlorine, bromine and iodine.

Where the term "lower alkyl" isused herein, it is to be understood to mean straight or branched chain alkyl groups containing from 1 to 4 carbon atoms.

Where the term "perhalo-(lower alkyl)" is used, it is to be understood to mean a lower alkyl group, as defined above, wherein each hydrogen is replaced by a halo atom, as defined above. Examples of perhalo-(lower alkyl) groups are trifluoromethyl and pentachloroethyl groups.

Where the term "halo-substituted phenyl" is used, it is to be understood to mean a phenyl group wherein one or more hydrogen is replaced by a halo atom, as defined above. Preferably two hydrogen are replaced by halo atoms, and the particularly preferred halo-substituted phenyl group is 2, 6-dichloro phenyl.

Where the term "lower aryl" is used herein, it is to be understood to mean monocyclic aromatic groups containing from 6 to 8 carbon atoms — for example, phenyl and toluyl groups.

By the term "agriculturally-acceptable salts", is meant any salt or salt-like derivative which preserves the activity, or substantially the activity, of the parent (that is, unsalified) compound, and which has no additional, undesirable effect on the plant being treated. It is to be understood that in some instances such salts may display an enhanced activity due to their being more readily assimilated by the plant being treated. Examples of the commonly employed salts are the metal salts of the acid function — such as the salts with sodium, calcium, aluminum, zinc, potassium, lithium, copper, molybdenum, manganese, magnesium, cobalt, selenium and iron — amine salts of the acid function — such as the diethanolamine salts — and salts of the heterocyclic nitrogen with mineral acids — such as the hydrochloride salts. There are a very large number of agriculturally acceptable salts suitable for use in this invention, as would readily be appreciated by one skilled in the art.

The particularly preferred compounds for use in the method of this invention are those compounds falling within the above general formula wherein $R^2$ is an electron-withdrawing group. That is to say, the preferred compounds are those wherein $R^2$ is selected from the group consisting of:
a. halo,
b. cyano,
c. nitro, and
d. perhalo-(lower alkyl).

Amongst these groups the particularly preferred electron-withdrawing groups are fluorine, chlorine and trifluoromethyl.

Examples of the preferred compounds for use in the invention are:
a. 2-chloro-4-quinoline carboxylic acid, and the methyl and ethyl esters thereof,
b. 5-chloro-4-quinoline carboxylic acid,
c. 2-trifluoromethyl-4-quinoline carboxylic acid,
d. 2-trifluoromethyl-8-fluoro-4-quinoline carboxylic acid,
e. 2-trifluoromethyl-6-fluoro-4-quinoline carboxylic acid,
f. 2,5-dichloro-4-quinoline carboxylic acid, and the methyl ester thereof,
g. 2-bromo-4-quinoline carboxylic acid,
h. 6-chloro-4-quinoline carboxylic acid,
i. 2-phenyl-4-quinoline carboxylic acid,
j. 2-methyl-6-bromo-4-quinoline carboxylic acid, and the ethyl ester thereof,
k. 5-chloro-2,4-quinoline dicarboxylic acid, and
l. 6-chloro-2,4-quinoline dicarboxylic acid.

In addition to the esters mentioned in the above list because of their outstanding activity, it may be stated generally that functional derivatives (as defined hereinbefore) of all these compounds will be found to be of particular interest.

The compounds used in the method of the present invention have been found to produce a wide variety of growth regulant effects in plants. The particular growth regulant effect produced in a plant depends, of course, on a number of variables, including the specific compound used, the concentration of the compound when applied to the plant, the formulation employed containing the compound, the time at which the compound is applied, and the type of plant species which is treated.

The mechanism by which these novel growth regulant compounds achieve their results in producing growth regulant effects in a plant is not precisely known. However, it is believed, although this invention is in no way limited by this theory, that the growth regulant effects are achieved by the use of these compounds as a result of some auxin inhibition that they induce in the plant.

The terms "growth regulant effect", "growth regulation", or words to that effect, are used in this specification and in the claims to mean a variety of plant responses which achieve promotion, inhibition, or modification of any physiological process within the plant. Such plant responses include a herbicidal action, the intention of which is to inhibit the growth of the plant by destroying or stunting its growth. Thus, the compounds used in the practice of this invention can be used in amounts which are phytotoxic or non-phytotoxic with respect to the plant being treated, depending on the result required.

The present invention contemplates the use of other compounds in conjunction with or in the presence of the compounds of this invention. These other compounds may be other growth regulators, including herbicides.

Amongst the wide variety of growth regulant effects which may be produced in plants using the method of the present invention are the following:
1. increase in yields;
2. inhibition of terminal growth and control of apical dominance;
3. promoting early yields in fruit;
4. promoting fruit set, particularly under adverse conditions;
5. blossom thinning;
6. delaying flowering;
7. parthenocarpic (seedless) fruit development;
8. resistance to freeze injury;
9. inhibiting, stunting, or destroying growth; and
10. male gametocide effects.

It is intended that as used herein terms such as "growth regulant effect" mean the achievement of any of the aforementioned ten categories of response, as well as any other promotion, inhibition, or modification of the plant or its seed or fruit.

Although the active compounds used in the method of this invention may, in some instances, be applied directly — in undiluted form — to the plant to be treated, it is much more usual for the active compounds to be formed into a composition with a suitable carrier. By the term "suitable" is meant that the carrier is chosen, having regard to the active compound employed and the plant being treated, so that it will not have any deleterious effect upon the method of the invention or the results obtained thereby.

Depending on how the composition is to be applied, the vehicle could be a solid (such as talc or vermiculite) or a liquid (such as water or a solvent) and it is believed to be within the competence of one skilled in the art to choose the appropriate vehicle for a particular compound and a particular application.

It is frequently most convenient and economic if the carrier used is water, and the composition is in the form of an aqueous solution. The compounds used in the method of the present invention are, however, soluble to varying degress in water. Therefore, as appropriate, they can be formed into aqueous solutions composed wholly or partially of water. Preferred solutions include those formed with water and, for example, acetone or methyl ethyl ketone, although practically any liquid solvent may be used, providing an effective growth regulating mixture can be formed. Where any particular derivative has limited solubility, it may be solubilized by the use of co-solvents and the like.

The precise amount of the compound used will, of course, depend upon a number of factors, including the specific compound employed, the particular plant species being treated, the time of treatment, and the desired growth regulant effect. By way of illustration, it may be said that from about 0.1 pounds to as much as 10 pounds/acre of the compounds will normally be applied in the method of this invention. However, it is preferred that the compounds used in the present invention be applied at rates of ⅛ to 4 pounds/acre, in any convenient manner. When applied in the form of an aqueous solution the total volume of solution applied may vary over a very wide range, but is conveniently from 1 to 150 gal/acre.

Although the preferred method of application of compounds used in the present invention is to apply it directly to the foliage and stems of plant, it has been found that the compounds may also be applied to the soil in which the plants are growing and that when applied in that manner the compounds will be root absorbed to a sufficient extent to result in plant responses in accordance with this invention.

The compounds of the present invention may be prepared by the following procedure.

The compounds of Formula I, wherein $R^4$ is a carboxyl group and $R^2$ is perhalo-(lower alkyl), e.g. trifluoromethyl, may be made by the basic synthesis route described by Dey and Joullie, J. Heterocyc. Chem., 2, 118 (1968) and Pinder and Burger, J. Med. Chem., 11, 267 (1968). For example:

Further, the compounds of Formula I, wherein $R^4$ is a carboxyl group and $R^2$ is a halo group, e.g. chlorine, are made by the basic synthesis route described by Campbell and Kerwin, J. Am. Chem. Soc., 68, 1837 (1946). For example:

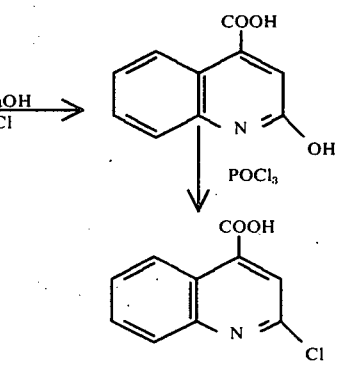

When it is desired to obtain substitution in the benzene ring an appropriately substituted aniline is used in place of the unsubstituted aniline used in preparing the isatin.

The compounds of Formula I, wherein $R^4$ is a carboxyl group, $R^2$ is hydrogen and there is substitution at the 5-, 6-, 7- or 8-position, may be made by the basic synthesis route described by Senear et al, J. Am. Chem. Soc. 68, 2695, (1946), which is illustrated by the following example:

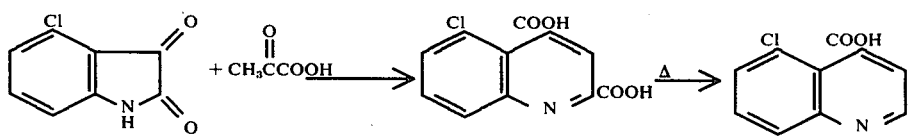

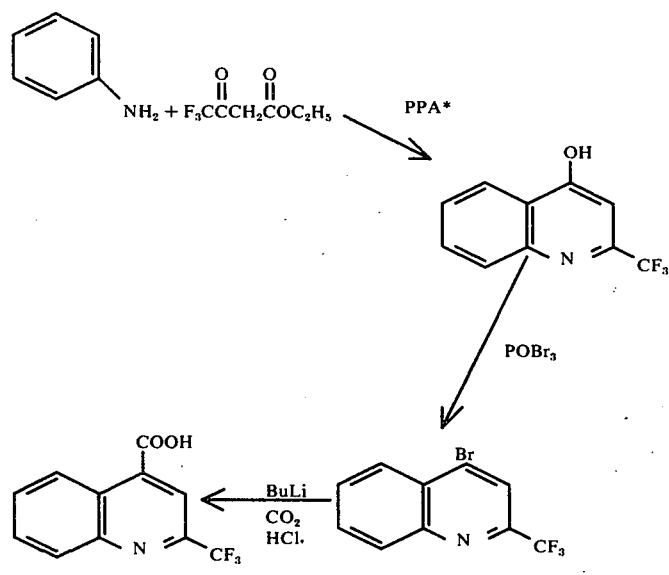

*polyphosphoric acid

When it is desired to obtain substitution in the benzene ring, i.e., in the 5-, 6-, 7- or 8-position, an appropriately substituted aniline is used in place of aniline.

In general, other compounds of Formula I are prepared as described by I. I. Krauch and W. Kuntz "Organic Name Reactions", John Wiley, N.Y., N.Y., 1969, P349; Robert C. Elderfield in "Heterocyclic Compounds", Vol. 4, Robert C. Elderfield, Ed., John Wiley, New York, N.Y., 1952, pp. 47–56; and R. B. Wagner and H. D. Zook, "Synthetic Organic Chemistry", John Wiley, New York, N.Y., 1965, p. 180.

The following example is illustrative of the preparation of typical formulations used in the present invention.

EXAMPLE 1

PREPARATION OF A COMPOSITON FOR USE IN THE METHOD OF THIS INVENTION

|  | % wt. |
|---|---|
| 2-chloro-4-quinoline carboxylic acid | 22.80 |
| diethanolamine | 11.31 |
| water | 65.89 |

2-chloro-4-quinoline carboxylic acid, diethanolomine and water were mixed until solution was achieved.

The pH of the solution obtained was 7.5.

The following evaluations are now given, though only by way of illustration, to show preferred compounds, amounts and techniques which may be employed in the method of this invention, and to demonstrate the surprising results obtained thereby.

Evaluations 1 to 18: Bean Inhibition

Seeds of Black Valentine snap beans were planted in four rows in greenhouse flats containing sterilized soil, watered and then placed in the greenhouse until ready for testing.

When the first trifoliolate leaf was just starting to expand, all terminal growth above the primary leaves was removed, leaving a 1 to 2 cm stub of internode growth. The plants were then thinned out so that in each flat there were 5 plants per row.

Ten mg. of each compound to be tested were dispersed in 1 ml. of melted lanolin. After the mixture had cooled, equal amounts of the dispersion were placed on the cut stub of each of ten plants. In a control treatment lanolin only was applied in the above manner.

After application, all flats were placed in a greenhouse for a period of 10–12 days, and at the end of this time all axillary branches from the primary leaf axes were removed, counted and weighed.

The amount of growth inhibition was determined by comparing the weights of axillary branches from the primary leaf axis obtained from each treatment to the control, and these results are expressed as percentage inhibition of these axillary branches in Table I below.

TABLE 1

| INHIBITION OF AXILLARY BRANCHING FROM PRIMARY LEAF AXIS | | |
|---|---|---|
| Evaluation | Compound | Inhibition (%) |
| 1 | 2-chloro-4-quinoline carboxylic acid methyl ester | 68 |
| 2 | 2-chloro-4-quinoline carboxylic acid ethyl ester | 40 |
| 3 | 2,5-dichloro-4-quinoline carboxylic acid | 94 |
| 4 | 6-chloro-2,4-quinoline dicarboxylic acid | 26 |
| 5 | 6-chloro-4-quinoline carboxylic acid | 63 |
| 6 | 2-methyl-6-bromo-4-quinoline carboxylic acid | 25 |
| 7 | 2-methyl-6-bromo-4-quinoline carboxylic acid ethyl ester | 37 |
| 8 | 2-trifluoromethyl-8-fluoro-4-quinoline carboxylic acid | 96 |
| 9 | 2-trifluoromethyl-4-quinoline carboxylic acid | 94 |
| 10 | 2-chloro-4-quinoline carboxylic acid | 42 |
| 11 | 2-phenyl-5-chloro-4-quinoline carboxylic acid | 26 |
| 12 | 5-chloro-4-quinoline carboxylic acid | 90 |
| 13 | 2-trifluoromethyl-6-fluoro-4-quinoline carboxylic acid | 100 |
| 14 | 2-bromo-4-quinoline carboxylic acid | 52 |
| 15 | 2-phenyl-4-quinoline carboxylic acid | 44 |
| 16 | 2-phenyl-4-quinoline carboxylic acid ethyl ester | 23 |
| 17 | 2-fluoro-4-cyano-quinoline | 32 |
| 18 | 4-quinoline carboxylic acid | 16 |

EVALUATIONS 19 TO 31

BEAN STIMULATION

A similar test to that performed in Evaluations 1 to 18 was carried out to investigate the stimulation of branching from the cotyledonary axils.

Black Valentine snap beans were seeded and treated as in Evaluations 1 to 18, and after 10–12 days the cotyledonary branches were removed, counted and weighed.

The amount of stimulation was determined by comparing the weights of the branches obtained from each treatment to the lanolin control.

The following compounds displayed stimulation of cotyledonary branching:

| Evaluation | |
|---|---|
| 19 | 2-chloro-4-quinoline carboxylic acid methyl ester; |
| 20 | 2-chloro-4-quinoline carboxylic acid ethyl ester; |
| 21 | 2,5-dichloro-4-quinoline carboxylic acid; |
| 22 | 6-chloro-2,4-quinoline dicarboxylic acid; |
| 23 | 6-chloro-4-quinoline carboxylic acid; |
| 24 | 2-methyl-6-bromo-4-quinoline carboxylic acid; |

-continued

| Evaluation | |
|---|---|
| 25 | 2-trifluoromethyl-8-fluoro-4-quinoline carboxylic acid; |
| 26 | 2-trifluoromethyl-4-quinoline carboxylic acid; |
| 27 | 2-chloro-4-quinoline carboxylic acid; |
| 28 | 2-phenyl-5-chloro-4-quinoline carboxylic acid; |
| 29 | 5-chloro-4-quinoline carboxylic acid; |
| 30 | 2-trifluoromethyl-6-fluoro-4-quinoline carboxylic acid; and |
| 31 | 2-bromo-4-quinoline carboxylic acid. |

EVALUATIONS 32 TO 47

TOMATO PARTHENOCARPY

Seeds of Pixie Hybrid Tomatoes were planted in greenhouse potting mix. When the seedlings had emerged and had two true leaves, they were transplanted into 7 inch pots. All pots were then placed in the greenhouse until the first flower on each plant was almost fully open.

Each compound under evaluation was dissolved in 5 ml of acetone plus 5 ml deionized water and applied to two plants as a foliar spray. Rates of 1 lb/acre and 2 lb/acre were employed.

After foliage had dried all plants were placed in a greenhouse where normal watering, insect control, etc. were maintained.

When the fruit had reached a suitable size they were removed separately from each plant. Each fruit was then cut open and the locules examined to determine seed production.

The results are expressed in terms of percentage of fruit showing parthenocarpy in Table 2 below:

EVALUATIONS 48 to 59

BEAN PARTHENOCARPY

Seeds of Dwarf Horticultural Dry Beans were planted in 4 inch square fibre pots containing sterilized soil, and placed in the greenhouse. After emergence of the bean plants all pots were thinned to contain one plant per pot.

When the first trifoliate of the bean plants had expanded, the compounds under test were applied as foliar sprays in a volume of 100 gal/acre.

All compounds were dissolved in 50% acetone plus 50% deionized water. Two replications were employed for each compound with rates of application of 2 lb/acre and 4 lb/acre.

After spraying, all plants were placed in the greenhouse under normal watering, fertilization, etc. When the beans were large enough to harvest they were removed separately from each plant and counted. Each pod was then cut in half lengthwise to determine presence or absence of seed.

The results expressed in terms of percentage of pods

TABLE 2

| | PARTHENOCARPY IN PIXIE HYBRID TOMATOES | |
|---|---|---|
| Evaluation | Compound | Parthenocarpy (%) |
| 32 | 5-chloro-2,4-quinoline dicarboxylic acid | 47 |
| 33 | 2-chloro-4-quinoline carboxylic acid methyl ester | 96 |
| 34 | 2-chloro-4-quinoline carboxylic acid ethyl ester | 91 |
| 35 | 2,5-dichloro-4-quinoline carboxylic acid | 100 |
| 36 | 2,5-dichloro-4-quinoline carboxylic acid methyl ester | 81 |
| 37 | 6-chloro-2,4-quinoline dicarboxylic acid | 25 |
| 38 | 6-chloro-4-quinoline carboxylic acid | 65 |
| 39 | 2-methyl-6-bromo-4-quinoline carboxylic acid | 95 |
| 40 | 2-methyl-6-bromo-4-quinoline carboxylic acid ethyl ester | 100 |
| 41 | 2-trifluoromethyl-8-fluoro-4-quinoline carboxylic acid | 69 |
| 42 | 2-trifluoromethyl-4-quinoline carboxylic acid | 97 |
| 43 | 2-chloro-4-quinoline carboxylic acid | 82 |
| 44 | 2-phenyl-5-chloro-4-quinoline carboxylic acid | 95 |
| 45 | 5-chloro-4-quinoline carboxylic acid | 68 |
| 46 | 2-trifluoromethyl-6-fluoro-4-quinoline carboxylic acid | 72 |
| 47 | 2-bromo-4-quinoline carboxylic acid | 78 | showing parthenocarpy, are expressed in Table 3 below:

TABLE 3

| | BEAN PARTHENOCARPY | |
|---|---|---|
| Evaluation | Compound | Parthenocarpy (%) |
| 48 | 5-chloro-2,4-quinoline dicarboxylic acid | 29 |
| 49 | 2-chloro-4-quinoline carboxylic acid methyl ester | 100 |
| 50 | 2-chloro-4-quinoline carboxylic acid ethyl ester | 41 |

TABLE 3-continued

BEAN PARTHENOCARPY

| Evaluation | Compound | Parthenocarpy (%) |
|---|---|---|
| 51 | 2,5-dichloro-4-quinoline carboxlic acid | 85 |
| 52 | 2,5-dichloro-4-quinoline carboxylic acid methyl ester | 25 |
| 53 | 6-chloro-4-quinoline carboxylic acid | 63 |
| 54 | 2-trifluoromethyl-8-fluoro-quinoline carboxylic acid | 100 |
| 55 | 2-trifluoromethyl-4-quinoline carboxylic acid | 100 |
| 56 | 2-chloro-4-quinoline carboxylic acid | 75 |
| 57 | 2-phenyl-5-chloro-4-quinoline carboxylic acid | 22 |
| 58 | 2-trifluoromethyl-6-fluoro-4-quinoline carboxylic acid | 90 |
| 59 | 2-bromo-4-quinoline carboxylic acid | 75 |

EVALUATION 60

Snap bean seeds (variety: Black Valentine) were planted in flats of vermiculite. Fifteen days after planting, the second internode was cut off to leave a stub approximately 1 cm long.

2-chloro-4-quinoline carboxylic acid was dispersed in 1 ml of warm lanolin. When cool, a small amount of this dispersion was placed on the freshly cut stub. The amounts of active material used are expressed in Tables 4 and 5 on a weight-to-volume basis. The check plants received a similar amount of lanolin containing no active material on the cut stub.

Fifteen plants were employed for each treatment, unless otherwise stated.

Readings were taken 12 days after treatment, at which time all axillary branches were counted and weighed.

The results are expressed in Table 4 as percent inhibition, based on the branch weight per plant compared to the check, at the primary leaf axil.

In addition, Table 5 shows the stimulation of branches at the cotyledonary axil for the various rates of treatment.

TABLE 4

PRIMARY LEAF AXIL INHIBITION

| 2-chloro-4-quinoline carboxylic acid (g/ml) | No. Plants | No. Branches | Total Branch wt. (gm) | Wt. per Branch (gm) | Wt. per Plant (gm) | (%) Inhibition |
|---|---|---|---|---|---|---|
| 0.005 | 16 | 30 | 6.22 | 0.21 | 0.39 | 33 |
| 0.01 | 15 | 29 | 2.61 | 0.09 | 0.18 | 69 |
| Check | 15 | 29 | 8.74 | 0.30 | 0.58 | — |

TABLE 5

COTYLEDONARY AXIL STIMULATION

| 2-chloro-4-quinoline carboxylic acid (g/ml) | No. Branches | Total Branch Wt. (gm) | Wt. per Branch (gm) | Wt. per Plant (gm) |
|---|---|---|---|---|
| 0.005 | 23 | 0.87 | 0.038 | 0.054 |
| 0.01 | 27 | 0.30 | 0.011 | 0.020 |
| Check | 0 | 0 | 0 | 0 |

EVALUATION 61

A. This evaluation demonstrates the use of a compound of this invention, 2-chloro-4-quinoline carboxylic acid, for producing parthenocarpic fruit development in tomatoes.

This trial was conducted on Walter tomatoes, a fresh market variety. The field was treated with a solution of the compound 61 days after it had been seeded. At the time of treatment several flowers on the first cluster were in blossom. Each treatment was replicated on 12 plants in a volume of 100-gals./acre, and a set of 12 plants was left untreated as a check.

Thirty-four days after treatment, all treated plants were growing vigorously, showed no evidence of inhibition, injury, or malformation, and had many blossoms (similar to checks). The plants treated with the 1 and 2 lbs./acre rate of active ingredient had larger flowers than the check plants. At this time the fruit was assessed for parthenocarpy, and it was observed that the fruit of all the treated plants appeared to contain fewer seeds than on the check plants.

The results of this test are shown in the following table, Table 6, and represent the averages per plant over the 12 replications.

TABLE 6

PARTHENOCARPY OF TOMATOES

(Average per Plant)

| Rate lb/A | No. fruit[1] | No. seedless | No. partly Seedless | No. seeded |
|---|---|---|---|---|
| 2.0 | 2.8 | 1.0 (39.4%) | 1.4 (50.0%) | 0.3 (10.6%) |
| 1.0 | 4.1 | 0.6 (14.6%) | 2.2 (53.6%) | 1.3 (31.8%) |
| 0.5 | 6.6 | 0.5 ( 7.6%) | 1.5 (22.8%) | 4.6 (69.6%) |

TABLE 6-continued

| PARTHENOCARPY OF TOMATOES (Average per Plant) | | | | |
|---|---|---|---|---|
| Rate lb/A | No. fruit[1] | No. seedless | No. partly Seedless | No. seeded |
| 0.25 | 7.2 | 0.4 ( 5.6%) | 2.1 (29.2%) | 4.7 (65.2%) |
| 0.125 | 13.6 | 0 ( 0%) | 1.0 ( 7.4%) | 12.6 (92.6%) |
| Control | 12.6 | 0 ( 0%) | 0.4 ( 3.2%) | 12.2 (96.8%) |

[1]Over 1 inch in diameter.

B. A further series of treatments was carried out on Walter tomatoes using various application rates of 2-chloro-4-quinoline carboxylic acid. Each treatment was replicated on 10 plants and was applied in a volume of 100-gals./acre. At the time of the treatment the tomato plants were large, and the first cluster had already set small fruit. The evaluation was carried out 35 days after treatment and at this time there was no evidence of any injury or malformation from any of the treatments. The results are shown in the following table, Table 7 for those that set subsequent to the treatment.

TABLE 7

| PARTHENOCARPY IN TOMATOES | |
|---|---|
| Rate (lb/A) | Results |
| 2.0 | fruit were 100% seedless |
| 1.0 | fruit were 10% seedless and 40% partly seedless |
| 0.5 | fruit were 5% seedless and 30% partly seedless |
| 0.25 | fruit were 20% partly seedless |
| 0.125 | fruit were 5% partly seedless |
| 0 | fruit were fully seeded |

C. A third series of tests was carried out on Walter tomato plants using various application rates of 2-chloro-4-quinoline carboxylic acid. The plants at the time of treatment were quite small (approximately 1-ft.) with a few blossoms on the first cluster just starting to open. Each treatment was replicated on 10 plants and was applied in a volume of 100-gals/acre. At the time of evaluation, the 2-lb./acre rate showed malformation on the leaves and new growth, the plants were considerably shorter (50%) than the controls, and very few flowers were present on the plants. At the 1-lb./acre rate there was slight malformation on the older leaves, the plants were slightly stunted (10–20%), but had approximately as many flowers as the check. The plants in the 0.5-lb./acre rate were similar in appearance to the controls. The results are shown in the following table, Table 8.

TABLE 8

| TOMATO PARTHENOCARPY Average per plant | | | | |
|---|---|---|---|---|
| Rate lb/A | No. fruit[1] | No. seedless | No. partly seedless | No. seeded |
| 2.0 | (no fruit present on any of the plants) | | | |
| 1.0 | (fruit just starting to set on a number of plants) | | | |
| 0.5 | 0.1 | 0 | 0.1 (100%) | 0 |
| 0.125 | 1.5 | 0 | 0.4 (26.7%) | 1.1 (73.3%) |
| Control | 1.9 | 0 | 0.1 ( 5.3%) | 1.8 (94.7%) |

[1]Over 1 inch in diameter.

On tomatoes, 2-chloro-4-quinoline carboxylic acid will cause parthenocarpic fruit development at rates of 1-2 lbs./acre. At lower rates, 0.125 lbs./acre, the compound causes only partial parthenocarpy; that is, one or more of the locules will contain seed. However, the degree of parthenocarpy appears to be inversely related to the percentage of fruit set, in that all rates giving some degree of parthenocarpy also have a lower fruit set and yield. This parthenocarpic fruit development took place under conditions of good pollination (the treated plants were in the middle of a nontreated field) and without any emasculation of the blossoms or removal of the stigmas on the style. It thus appears that 2-chloro-4-quinoline carboxylic acid, in addition to stimulating the growth and development of the ovary, is also having an effect on pollen germination, pollen tube growth, gamete formation, gamete movement in the pollen tubes, or on the actual formation and development of a fertilized egg, or on the development of the ovule itself.

EVALUATION 62

This evaluation demonstrates the use of a compound of this invention, 2-chloro-4-quinoline carboxylic acid for producing increased fruit set and parthenocarpic fruit development in tomatoes.

A growth chamber experiment was established to study the effects of 2-chloro-4-quinoline carboxylic acid on promoting tomato fruit set under high temperatures. At high night temperatures, tomatoes normally set fruit very sparingly or not at all.

Seedlings of the tomato variety Pixie Hybrid were transplanted into 7 inch pots using a potting mixture consisting of equal parts of soil, sand, and perlite. Three teaspoons of Osmocote slow-release fertilizer were added to each pot. These pots were kept in a greenhouse until well-defined floral buds were visible. At this time uniform plants were selected and placed in the Growth Chamber.

Chamber conditions were as follows:
Temperature — 90° F day; 80° F night
Photoperiod — 15 hours
Light Intensity — 3,600 foot candles At the appropriate stage of floral development, the plants were taken out of the chamber to be sprayed. 2-chloro-4-quinoline carboxylic acid was dissolved in a solution containing 50% acetone plus 50% water.

Foliar sprays were applied at the rate of 150 gallons of this solution per acre as an overall plant spray. The treatments were made at three stages at intervals of approximately ten days. Three replications were employed for each treatment.

All readings were taken 9 days after the final treatment, by harvesting, and weighing fruit from each plant. The results are summarized in Table 9 below.

TABLE 9
MEANS FOR THREE REPLICATIONS

| Rate lb/A | Treatment[a] | No. tomatoes per plant | No. parthen. per plant | Total fruit weight per plant (gm) | Weight per fruit (gm) |
|---|---|---|---|---|---|
| ½ | 1 | 0 | — | 0 | 0 |
| 1 | 1 | 0.3 | 0.3 | 1.92 | 6.40 |
| Check | — | 0 | — | 0 | 0 |
| ½ | 2 | 8.0 | 8.0 | 48.5 | 6.02 |
| 1 | 2 | 6.0 | 6.0 | 42.88 | 7.15 |
| Check | — | 0 | — | 0 | 0 |
| ½ | 3 | 2.0 | 2.0 | 0.80 | 0.40 |
| 1 | 3 | 0 | — | 0 | 0 |

[a]
Treatment 1 - Applied when flowers in 1st cluster were at light-bud stage.
Treatment 2 - Applied when first flower was open
Treatment 3 - Applied when 2-3 clusters had open flowers, some past anthesis.

Temperatures of 90° F day and 80° F night with a 15-hour photo-period completely prevented fruit set in untreated checks. However, when 2-chloro-4-quinoline carboxylic acid was applied when the first flower was open (Treatment 2), good yields of fruit were set, all of which were completely parthenocarpic.

The above compound was also applied at an earlier stage (Treatment 1) when the first cluster was visible but individual flowers were showing no yellow color. When the compound was applied at a latter stage (Treatment 3) with 2-3 clusters showing both open flowers and flowers past anthesis, fruit was again set. This fruit, as would be expected, was quite small but also parthenocarpic.

From this trial it is apparent that 2-chloro-4-quinoline carboxylic acid was effective in promoting fruit set under adverse conditions.

EVALUATION 63

This evaluation demonstrates the use of a compound of this invention, 2-chloro-4-quinoline carboxylic acid, for producing increased fruit set and parthenocarpic fruit development in tomatoes.

A growth chamber experiment was initiated to determine the effectiveness of 2-chloro-4-quinoline carboxylic acid on tomatoes grown under high temperatures.

Normally, tomatoes grown under high night temperatures will set little if any fruit. The compound of the invention, applied in the first flower stage, overcame the effects of high temperatures on tomato fruit set. Application at the 2–3 cluster stage wer also effective. The fruit from all the treated plants was parthenocarpic.

The results are summarized below in Table 10.

TABLE 10

| Compound | Stage[1] | Rate lb/A | Fruit per Plant | Fruit weight per plant (gm) | Parthenocarpic fruit per plant |
|---|---|---|---|---|---|
| 2-chloro-4-quinoline carboxylic acid | 1 | ½ | 0.3 | 1.9 | 0.3 |
|  |   | 1 | 0 | 0 | 0 |
| " | 2 | ½ | 5.0 | 36.3 | 5.0 |
|  |   | 1 | 4.7 | 32.4 | 4.7 |
| " | 3 | ½ | 6.7 | 3.7 | 6.7 |
|  |   | 1 | 0.3 | 0.1 | 0.3 |
| Check | — | — | 0 | 0 | — |

Variety: Pixie Hybrid
Volume: 150 gal/A
Method: Foliar spray
Conditions: 90° F day; 80° F night Stage[1]
1 - buds visible on 1st cluster with no color evident
2 - first open flower on 1st cluster
3 - 2-3 clusters with open flowers; some post anthesis.

EVALUATION 64

This evaluation demonstrates the use of a compound of this invention, 2-trifluoromethyl-4-quinoline carboxylic acid, for producing increased fruit set, increased fruit yield, promotion of early yields, and parthenocarpic fruit development in tomatoes.

A greenhouse trial was established to measure fruit set and yield in tomatoes. As can be seen from the following table (Table 11), not only were the number and total weight of fruit more than doubled, but also the fruits were more mature and completely seedless. In this trial results were taken from the first cluster only.

TABLE II

| Compound | Rate lb/A | Fruit per Plant | Total fruit weight per plant (gm) | Weight per fruit (gm) | Pink and Red Fruit per plant | Parthenocarpy |
|---|---|---|---|---|---|---|
| 2-trifluoro-methyl-4-quinoline carboxylic acid | ⅛ | 1.5 | 99.9 | 66.6 | 1.0 | — |
| " | ¼ | 2.0 | 125.8 | 62.9 | 2.0 | Yes |
| " | ½ | 3.0 | 154.7 | 51.6 | 1.0 | Yes |
| " | 1 | 3.0 | 158.4 | 52.8 | 2.0 | Yes |
| Control | — | 0.75 | 45.9 | 61.2 | 0.25 | No |

EVALUATION 65

This evaluation demonstrates the use of a compound of this invention, 2-trifluoromethyl-4-quinoline carboxylic acid, for producing promotion of early yields and parthenocarpic fruit development in tomatoes.

A field trial was conducted on tomatoes. As can be seen from the following table; applications of a 2-trifluoromethyl-4-quinoline carboxylic acid at the first cluster stage advanced the harvest period by two weeks. Similar responses were observed from later applications at the 2–3 cluster stage. It was also noted that treated fruit from the first 4–5 harvests showed a high percentage of parthenocarpy.

EVALUATION 67

This evaluation demonstrates the use of a compound of the invention, 2-chloro-4-quinoline carboxylic acid for producing inhibition of terminal growth and delay of flowering.

In this trial the watermelon plants were treated with 2-chloro-4-quinoline carboxylic acid at various rates. At the time of treatment the plants were in the young seedling stage (first true leaf stage). Each treatment was replicated on 10 plants and was applied in a volume of 100-gal./acre. In no case did any of the treatments cause any malformation. The results were evaluated 35 days after treatment and are shown in the following table.

TABLE 12

| Time from First Harvest (days) | Check | Yield/plant (oz) 2-trifluoromethyl-4-quinoline carboxylic acid | | | | | |
|---|---|---|---|---|---|---|---|
| | | ¼ lb/A | ½ lb/A | 1.0 lb/A | ⅛ lb/A | ¼ lb/A | ½ lb/A |
| 0 | 2.0 | 11.2 | 6.7 | 10.5 | 0.8 | 4.2 | 2.4 |
| 5 | 5.0 | 15.4 | 12.1 | 8.3 | 19.4 | 11.0 | 16.2 |
| 12 | 18.8 | 0.4 | 3.6 | 7.7 | 14.0 | 25.2 | 21.4 |
| 19 | 21.4 | 1.0 | 0 | 1.1 | 13.2 | 29.8 | 14.6 |
| 26 | 56.5 | 5.9 | 1.1 | 0 | 28.4 | 15.6 | 20.4 |
| 32 | 41.5 | 30.6 | 15.6 | 14.0 | 8.0 | 0.8 | 1.0 |
| 39 | 8.8 | 27.8 | 25.2 | 16.4 | 3.8 | 0.6 | 0 |
| 46 | 8.1 | 12.0 | 13.8 | 14.0 | 7.0 | 4.6 | 1.0 |
| | 162.1 | 104.3 | 78.1 | 72.0 | 94.6 | 91.8 | 77.0 |
| | | Applied at first cluster stage | | | Applied at 2 to 3 cluster stage | | |

EVALUATION 66

This evaluation demonstrates the use of a compound of this invention, 2-trifluoromethyl-4-quinoline carboxylic acid, for producing parthenocarpic fruit development in cucumbers.

A growth chamber trial was established to study the effects of 2-trifluoromethyl-4-quinoline carboxylic acid on gynoecious variety of cucumber. Since this type of cucumber produces female flowers only, no fruit should set due to lack of pollination. As can be seen in the following table, fruit set without fertilization with rates of the compound above 1/16 lb/acre. These fruit were parthenocarpic. Fruit 4 centimeters in length and smaller always abort from this variety.

TABLE 14

| Rate (lb/A) | Results |
|---|---|
| 2.0 | vines 1.0–1.5 ft., no open flowers, very small flower buds |
| 1.0 | vines 2.0 ft., no open flowers, very small flower buds |
| 0.25 | vines 2.0 ft., no open flowers, normal flower buds |
| 0.125 | vines 2.0 ft., no open flowers, normal flower buds |
| Check | vines 2.0 ft., male blossoms starting to open |

High rates (2-lb/acre) gave a temporary inhibition of vine growth, at least at the early seedling stage.

TABLE 13

| Compound | Rate lb/A | Final plant Height (cm) | Fruit over 4 cm long (per plant) | Fruit Weight per plant (gm) | Ave. length of fruit over 4 cm long (cm) | Total fruit parth. per plant |
|---|---|---|---|---|---|---|
| 2-trifluoro-methyl-4-quinoline carboxylic acid | 1/16 | 44.4 | 0 | 0 | 0 | 0 |
| " | 1/8 | 40.7 | 0.6 | 60.0 | 11.0 | 0.6 |
| " | 1/4 | 39.5 | 0.6 | 50.9 | 10.3 | 0.6 |
| " | 1/2 | 32.5 | 1.3 | 44.5 | 7.6 | 1.3 |
| Control | — | 43.4 | 0 | 0 | 0 | 0 |

EVALUATION 68

This evaluation demonstrates the use of a compound of this invention, 2-chloro-4-quinoline carboxylic acid for producing male sterility in corn.

Pre-germinated seeds of Golden Midget corn were potted in 3 inch pots. After 13 days the plants were transplanted into 7 inch pots with sterilized soil.

All treatments were made with 2-chloro-4-quinoline carboxylic acid, in a volume of approximately 150-gals./acre.

The stage of application and spray dates were as follows:

2-leaf stage — 4 days after transplanting
4-leaf stage — 8 days after transplanting
6-leaf stage — 19 days after transplanting
9-10-leaf stage — 24 days after transplanting Two replications were obtained with one plant per replication.

Observations were made 70 days after transplanting. The following table illustrates results obtained for each stage of chemical application:

TABLE 15

| Rate lb/A | Application stage | Ears per plant | Kernels per ear | Visual Tassel Development |
|---|---|---|---|---|
| 2 | 2L | 1.0 | 118.0 | normal |
| 4 | 2L | 4.5 | 0.7 | none present |
| 2 | 4L | 0.5 | 45.0 | normal |
| 4 | 4L | 1.5 | 13.0 | reduced pollen production |
| 2 | 6L | 3.0 | 16.0 | reduced pollen production |
| 4 | 6L | 1.0 | 61.5 | reduced pollen production |
| 2 | 10L | 2.0 | 78.0 | normal |
| 4 | 10L | 1.5 | 69.0 | normal |
| check | — | 1.0 | 119.0 | normal |

[1]Application stage:
2L = two-leaf stage
4L = four-leaf stage
6L = six-leaf stage
10L = ten-leaf stage Foliar applications of this compound to corn in the twoleaf stage, as can be seen from the above table, completely eliminated anther development at a rate of 4-lb./acre. Although all plants were segregated, two ears from this treatment produced an average of three kernels per ear. Pollination probably occurred from wind-blown pollen from another plant. This would indicate the silks were not affected by treatment and were still receptive to pollen.

Applications were also made at the four-leaf, six-leaf and ten-leaf stage of plant development. Although a complete absence of anthers and pollen production was not obtained, a reduction in the number of kernels per ear was noted. This could indicate a reduction in anther and pollen production per plant.

There was also an increase in the number of ears on the treated plants.

EVALUATION 69

This evaluation demonstrates use of a compound of this invention, 2-trifluoromethyl-4-quinoline carboxylic acid, for producing male sterility in wheat.

Seed of Neepawa spring wheat were planted in 7 inch pots of sterilized soil.

The compound of the invention was applied 20, 35 and 45 days after planting in a volume of 150 gals./acre using a solvent system of 50% water.

Three replications were obtained with three plants per replication.

As soon as the seed head was visible, but well before flowering, a total of 10–15 heads were placed in bags. The heads remained in these bags until readings were made 109 days after planting. At this time heads were removed and the number of seeds per head counted.

Check plants were also treated in the above manner.

The following table (Table 16) illustrates results obtained for each compound tested.

TABLE 16

| Compound | Application Stage | Rate lb/A | Kernels per head | % Sterility | % Seedless heads |
|---|---|---|---|---|---|
| Check | — | — | 23.5 | — | 0 |
| 2-trifluoromethyl-4-quinoline carboxylic acid | 1–2 joint stage | 2 | 5.3 | 77 | 13 |
| 2-trifluoromethyl-4-quinoline carboxylic acid | 1–2 joint stage | 4 | 2.4 | 90 | 33 |
| 2-trifluoromethyl-4-quinoline carboxylic acid | last leaf visible | 4 | 5.7 | 76 | 46 |

Foliar application of 2-trifluoromethyl-4-quinoline carboxylic acid to spring wheat at the one to two node stage of growth, as can be seen from the above table, produced 75–90% male sterility. No visible malformation of the head was apparent. On heads not bagged, kernels were produced, indicating the female parts were still receptive to pollen.

Applications of 2-trifluoromethyl-4-quinoline carboxylic acid at the last leaf stage produced 76% male sterility, again with no apparent head malformation. At this stage, the number of heads containing no seed was approximately 50% compared to 33% at the one to two node stage.

EVALUATION 70

This evaluation demonstrates the use of a compound of this invention, 2-chloro-4-quinoline carboxylic acid, for producing a reduction in the amount of pollen production in corn.

Corn was treated with the compound of this invention, when the plants were 1.0–1.5 feet tall and in the 5th leaf stage. Each treatment was replicated on 20 plants and was applied in a volume of 100-gal/acre. Treatments were applied at rates of 4, 2, 1, and 0.5-lb/acre. The plants were evaluated 35 days after treatment, when the treatments appeared similar to the controls. The plants were in tassel, shedding pollen, the silks were out and appeared receptive. At the 4-lb/acre rate there did not appear to be much pollen in the anthers. What pollen was present did not appear normal.

EVALUATION 71

This evaluation demonstrates the use of a compound of this invention, 2-chloro-4-quinoline carboxylic acid, for producing a male sterile plant.

2-chloro-4-quinoline caroxylic acid was applied to Xanthii tobacco plants which had been topped prior to spraying. A rate of 100 mg/plant resulted in approximately 30% sucker inhibition. After the plants had remained for some time, it was noticed the treated plants appeared to have no male parts in the flower.

EVALUATION 72

This evaluation demonstrates the use of compounds of this invention, 2-trifluoromethyl-4-quinoline carboxylic acid and 2-chloro-4-quinoline carboxylic acid, for producing inhibition of growth in woody plants.

A field trial was established to study the effectiveness of both 2-trifluoromethyl-4-quinoline carboxylic acid and 2-chloro-4-quinoline carboxylic acid as woody plant growth inhibitors. Both materials were applied to 5 species of trees as a cut-stub treatment similar to the treatment described for Evaluation 1 to 18 using a formulation containing 5% active ingredient.

TABLE 17

| Species | Percent Inhibition | |
|---|---|---|
| | 2-trifluoromethyl-4-quinoline carboxylic acid | 2-chloro-4 quinoline carboxylic acid |
| Pin Oak | 53 | 39 |
| Chinese Elm | 51 | 16 |
| White Ash | 54 | 23 |
| Norway Maple | 100 | 100 |
| Sycamore | 31 | 6 |
| AVERAGE | 58% | 35% |

EVALUATION 73

This evaluation demonstrates the use of several quinoline derivatives for promoting resistance to freeze injury.

Zucchini squash was planted in 3 inch pots in vermiculite, 5 milliliters of solution were applied as a soil drench to each pot. There were sixteen pots per treatment. The zucchini squash was put through a 24 hour freezing cycle. The freezing cycle has a minimum temperature of 24° F and there were seven hours in which the temperature was below 30° F.

The compounds were applied in a formulation consisting of from 25 to 30% acetone and water (except as noted).

The following table, Table 18, illustrates results obtained for each compound tested.

TABLE 18

| Compound | % Survival Check | % Survival Treated | PPM (active ingredient) | Comments |
|---|---|---|---|---|
| 5-chloro-4-quinoline carboxylic acid | 25% | 56% | 1000 | Applied at two leaf stage |
| 2-bromo-4-quinoline carboxylic acid | 38% | 50% | 1000 | Applied at two leaf stage |
| 7-fluoro-4-quinoline carboxylic acid | 44% | 50% | 1000 | Applied at two leaf stage |
| 2-trifluoromethyl-4-quinoline carboxylic acid | 0% | 12% | 500 | Applied at two leaf stage, 75% acetone and 25% water |
| 2-trifluoromethyl-4-quinoline carboxylic acid | 0% | 25% | 250 | Applied at two leaf stage, 75% acetone and 25% water |
| 7-chloro-2-trifluoromethyl-4-quinoline carboxylic acid | 0% | 19% | 1000 | Applied at two leaf stage |
| 7-chloro-2-trifluoromethyl-4-quinoline carboxylic acid | 12% | 50% | 1000 | Applied at one and a half to two leaf stage |
| 7-trifluoromethyl-4-quinoline carboxylic acid, ethyl ester | 12% | 19% | 1000 | Applied at one and a half to two leaf stage |
| 6-fluoro-2-trifluoromethyl-4-quinoline carboxylic acid | 6% | 19% | 1000 | Applied at one and a half to two leaf stage |
| 7-chloro-4-quinoline carboxylic acid | 0% | 12% | 1000 | Applied at two leaf stage |
| 4-quinoline carboxylic acid | 0% | 12% | 1000 | Applied at two leaf stage |
| 2-chloro-4-quinoline carboxylic acid | 0% | 19% | 1000 | Applied at two leaf stage |

We claim:

1. A method for producing a resistance to freeze injury in a plant which comprises applying to the plant an effective amount, with respect to the plant being treated, of a compound selected from the group consisting of:

(A) 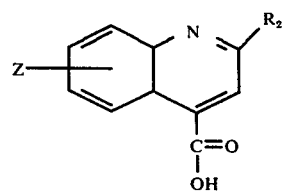

wherein Z is selected from the group consisting of:
  a. hydrogen,
  b. chlorine, and
  c. fluorine;
$R_2$ is selected from the group consisting of:
  a. hydrogen,
  b. trifluoromethyl,
  c. bromine, and
  d. chlorine; and
B. agriculturally acceptable salts of (A) selected from the group consisting of:
  a. alkaline earth metal salts,
  b. mono-, di or tri alkylamine salts of 1 to 3 carbon atoms,
  c. mono- , di or tri- alkanolamine salts of 1 to 3 carbon atoms, and
  d. acid addition salts of a non-phytotoxic acid.

2. The method of claim 1, wherein the compound is 2-chloro-4-quinoline carboxylic acid.

3. The method of claim 1, wherein the compound is 2-trifluoromethyl-4-quinoline carboxylic acid.

4. The method of claim 1, wherein the effective amount is from about 0.1 to about 10 lbs/acre.

5. The method of claim 1, wherein the plant is zucchini squash.

6. A method for producing parthenocarpic fruit development in a plant which comprises applying to the plant an effective amount, with respect to the plant being treated, a compound selected from the group consisting of:

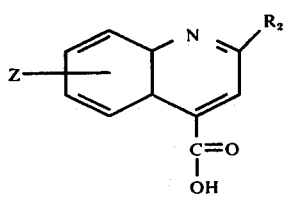
(A)

wherein, Z is selected from the group consisting of:
a. hydrogen,
b. chlorine,
c. fluorine, and
d. bromine;

$R_2$ is selected from the group consisting of:
a. hydrogen,
b. chlorine,
c. bromine,
d. trifluoromethyl,
e. phenyl,
f. methyl, and
g. carboxyl; and B. agriculturally acceptable salts of (A) selected from the group consisting of:
a. alkaline earth metal salts,
b. mono-, di- or tri- alkylamine salts of 1 to 3 carbon atoms,
c. mono-, di- or tri- alkanolamine salts of 1 to 3 carbon atoms, and
d. acid addition salts of a non-phytotoxic acid.

7. The method of claim 6, wherein the compound is 2-chloro-4-quinoline carboxylic acid.

8. The method of claim 6, wherein the compound is 2-trifluoromethyl-4-quinoline carboxylic acid.

9. The method of claim 6, wherein the effective amount is from about 0.1 to about 10 pounds per acre.

10. The method of claim 6, wherein the plant is tomato.

11. The method of claim 6, wherein the plant is cucumber.

12. The method of claim 6, wherein the plant is bean.

13. A method for producing a male gametocide effect in a plant which comprises applying to the plant an effective amount, with respect to the plant being treated, of a compound selected from the group consisting of:

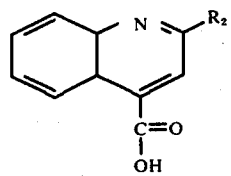
(A)

wherein $R_2$ is selected from the group consisting of:
a. chlorine, and
b. trifluoromethyl; and B. agriculturally acceptable salts of (A) selected from the group consisting of:
a. alkaline earth metal salts,
b. mono-, di- or tri- alkylamine salts of 1 to 3 carbon atoms,
c. mono-, di- or tri- alkanolamine salts of 1 to 3 carbon atoms, and
d. acid addition salts of a non-phytotoxic acid.

14. The method of claim 13, wherein the compound is 2-chloro-4-quinoline carboxylic acid.

15. The method of claim 13, wherein the compound is 2-trifluoromethyl-4-quinoline carboxylic acid.

16. The method of claim 13, wherein the effective amount is from about .1 to about 10 pounds per acre.

17. The method of claim 13, wherein the plant is corn.

18. The method of claim 13, wherein the plant is wheat.

19. The method of calim 13, wherein the plant is tobacco.

20. A method for producing a delay in flowering in a plant which comprises applying to the plant an effective amount, with respect to the plant being treated, of a compound selected from the group consisting of:
A. 2-chloro-4-quinoline carboxylic acid; and
B. agriculturally acceptable salts of (A) selected from the group consisting of:
a. alkaline earth metal salts,
b. mono-, di- or tri- alkylamine salts of of 1 to 3 carbon atoms,
c. mono-, di or tri- alkanolamine salts of of 1 to 3 carbon atoms, and
d. acid addition salts of a non-phytotoxic acid.

21. The method of claim 20, wherein the compound is 2-chloro-4-quinoline carboxylic acid.

22. The method of claim 20, wherein the effective amount is from about .1 to about 10 pounds per acre.

23. The method of claim 20, wherein the plant is a watermelon plant.

24. A method for producing blossom thinning in a plant, which comprises applying to the plant an effective amount, with respect to the plant being treated, of a compound selected from the group consisting of:
A. 2-chloro-4-quinoline carboxylic acid; and
B. agriculturally acceptable salts of (A) selected from the groups consisting of:
a. alkaline earth metal salts,
b. mono-, di- or tri- alkylamine salts of 1 to 3 carbon atoms,
c. mono-, di- or tri- alkanolamine salts of 1 to 3 carbon atoms, and
d. acid addition salts of a non-phytotoxic acid.

25. The method of calim 24, wherein the compound is 2-chloro-4-quinoline carboxylic acid.

26. The method of claim 24, wherein the effective amount is from about .1 to about 10 pounds per acre.

27. The method of claim 24, wherein the plant is tomato.

28. A method for producing a promotion of fruit set in a plant which comprises applying to the plant an effective amount, with respect to the plant being treated, of a compound selected from the group consisting of:

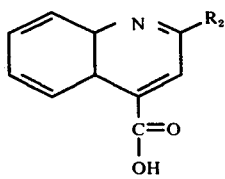

(A)

wherein R$_2$ is selected from the group consisting of:
 a. chlorine, and
 b. trifluoromethyl; and
B. agriculturally acceptable salts of (A) selected from the group consisting of:
 a. alkaline earth metal salts,
 b. mono-, di- or tri- alkylamine salts of 1 to 3 carbon atoms,
 c. mono-, di- or tri- alkanolamine salts of 1 to 3 carbon atoms, and
 d. acid addition salts of a non-phytotoxic acid.

29. The method of claim 28, wherein the compound is 2-chloro-4quinoline carboxylic acid.

30. The method of claim 28, wherein the compound is 2-trifluoromethyl-4-quinoline carboxylic acid.

31. The method of claim 28, wherein the effective amount is from about 0.1 to about 10 pounds per acre.

32. The method of claim 28, wherein the plant is tomato.

33. A method for producing the promotion of early yields in a plant which comprises applying to the plant in effective amount, with respect to the plant being treated, of a compound selected from the group consisting of:

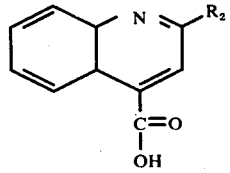

(A)

wherein R$_2$ is selected from the group consisting of:
 a. chlorine, and
 b. trifluoromethyl; and
B. agriculturally acceptable salts of (A) selected from the group consisting of:
 a. alkaline earth metal salts,
 b. mono-, di- or tri- alkylamine salts of 1 to 3 carbon atoms,
 c. mono-, di- or tri- alkanolamine salts of 1 to 3 carbon atoms, and
 d. acid addition salts of a non-phytotoxic acid.

34. The method of claim 33, wherein the compound is 2-chloro-4-quinoline carboxylic acid.

35. The method of claim 33, wherein the effective amount is from about 0.1 to about 10 pounds per acre.

36. The method of claim 33, wherein the plant is tomato.

37. A method for controlling apical dominance in a plant which comprises applying to the plant an effective amount, with respect to the plant being treated, of a compound selected from the group consisting of:

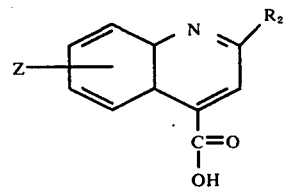

(A)

wherein, Z is selected from the group consisting of:
 a. hydrogen,
 b. chlorine,
 c. fluorine, and
 d. bromine;
R$_2$ is selected from the group consisting of:
 a. hydrogen,
 b. chlorine,
 c. bromine,
 d. trifluoromethyl,
 e. phenyl,
 f. methyl, and
 g. carboxyl; and
B. agricultrually acceptable salts of (A) selected from the group consisting of:
 a. alkaline earth metal salts,
 b. mono-, di- or tri- alkylamine salts of 1 to 3 carbons atoms,
 c. mono-, di- or tri- alkanolamine salts of 1 to 3 carbon atoms, and
 d. acid addition salts of non-phytotoxic acid.

38. The method of claim 37, wherein the compound is 2-chloro-4-quinoline carboxylic acid.

39. The method of claim 37, wherein the compound is 2-trifluoromethyl-4-quinoline carboxylic acid.

40. The method of claim 37, wherein the effective amount is from about .1 to about 10 pounds per acre.

41. The method of claim 37, wherein the plant is beans.

42. A method for producing an inhibition of terminal growth in a plant which comprises applying to the plant an effective amount, with respect to the plant being treated, of a compound selected from the group consisting of:

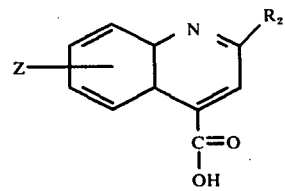

(A)

wherein, Z is selected from the group consisting of:
 a. hydrogen,
 b. chlorine,
 c. fluorine, and
 d. bromine;
R$_2$ is selected from the group consisting of:
 a. hydrogen,
 b. chlorine, c. bromine,
d. trifluoromethyl,
e. phenyl,
f. methyl, and
g. carboxyl; and B. agriculturally acceptable salts of (A) selected from the group consisting of:
a. alkaline earth metal salts,
b. mono-, di- or tri- alkylamine salts of 1 to 3 atoms,
c. mono-, di- or tri- alkanolamine salts of 1 to 3 carbon atoms, and
d. acid addition salts of a non-phytotoxic acid.

43. The method of claim 42, wherein the compound is 2-chloro-4-quinoline carboxylic acid.

44. The method of claim 42, wherein the compound is 2-trifluoromethyl-4-quinoline carboxylic acid.

45. The method of claim 42, wherein the effective amount is from about 0.1 to about 10 pounds per acre.

46. The method of claim 42, wherein the plant is beans.

47. A method for producing an increase in yield in a plant which comprises applying to the plant an effective amount, with respect to the plant being treated, of a compound selected from the group consisting of:

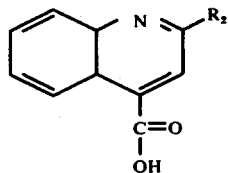
(A)

wherein $R_2$ is selected from the group consisting of:
a. chlorine, and
b. trifluoromethyl; and B. agriculturally acceptable salts of (A) selected from the group consisting of:
a. alkaline earth metal salts,
b. mono-, di- or tri-alkylamine salts of 1 to 3 carbon atoms,
c. mono-, di- or tri- alkanolamine salts of 1 to 3 carbon atoms, and
d. acid addition salts of a non-phytotoxic acid.

48. The method of claim 47, wherein the compound is 2-chloro-4-quinoline carboxylic acid.

49. The method of claim 47, wherein the compound is 2-trifluoromethyl-4-quinoline carboxylic acid.

50. The method of claim 47, wherein the effective amount is from about 0.1 to about 10 pounds per acre.

51. The method of claim 47, wherein the plant is tomato.

52. The method of claim 47, wherein the plant is cucumbers.

53. A method for producing an inhibition of growth of a woody plant which comprises applying to the plant an effective amount, with respect to the plant being treated, of a compound selected from the group consisting of:

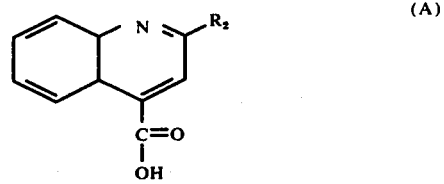
(A)

wherein $R_2$ is selected from the group consisting of:
a. chlorine, and
b. trifluoromethyl; and B. agriculturally acceptable salts of (A) selected from the group consisting of:
a. alkaline earth metal salts,
b. mono-, di- or tri- alkylamine salts of 1 to 3 carbon atoms,
c. mono-, di- or tri- alkanolamine salts of 1 to 3 carbon atoms, and
d. acid addition salts of a non-phytotoxic acid.

54. The method of claim 63, wherein the compound is 2-chloro-4-quinoline carboxylic acid.

55. The method of claim 53, wherein the compound is 2-trifluoromethyl-4-quinoline carboxylic acid.

56. The method of claim 53, wherein the effective amount is from about 0.1 to about 10 pounds per acre.

* * * * *